(12) United States Patent
Hayashi et al.

(10) Patent No.: US 7,893,004 B2
(45) Date of Patent: Feb. 22, 2011

(54) OXIDATION REACTION CATALYST AND PROCESS FOR PRODUCING A COMPOUND USING THE SAME

(75) Inventors: Masahiko Hayashi, Kobe (JP); Yuka Kawashita, Kobe (JP); Juichi Yanagi, Osaka (JP); Isao Hamasaki, Osaka (JP)

(73) Assignee: Japan Envirochemicals, Ltd., Osaka (JP)

( * ) Notice: Subject to any disclaimer, the term of this patent is extended or adjusted under 35 U.S.C. 154(b) by 144 days.

(21) Appl. No.: 11/661,822

(22) PCT Filed: Sep. 5, 2005

(86) PCT No.: PCT/JP2005/016227

§ 371 (c)(1),
(2), (4) Date: Mar. 2, 2007

(87) PCT Pub. No.: WO2006/028035

PCT Pub. Date: Mar. 16, 2006

(65) Prior Publication Data

US 2007/0265475 A1    Nov. 15, 2007

(30) Foreign Application Priority Data

Sep. 6, 2004    (JP) .............................. 2004-258005

(51) Int. Cl.
  *B01J 21/18* (2006.01)
(52) U.S. Cl. ........................ 502/180; 502/100; 568/300
(58) Field of Classification Search ....................... None
  See application file for complete search history.

(56) References Cited

U.S. PATENT DOCUMENTS 3,969,398 A * 7/1976 Hershman .................... 562/17

FOREIGN PATENT DOCUMENTS

JP    11-49717    2/1999

OTHER PUBLICATIONS

Hu, Z. et al., Novel activation process for preparing highly microporous and mesoporous activated carbons, 2001, Carbon, vol. 39, pp. 877-886.*
Gonzalez-Serrano et al., Development of Porosity upon Chemical Activatin of Draft lignin with ZnCl2, 1997, Industrial & Engineering Chemistry Research, vol. 36, No. 11, pp. 4832-4838.*
Teng et al., Preparation of Activated Carbons from Bitiminous coals with Zinc Chloride Activation, 1998, Industrial & Engineering Chemistry Researcy, vol. 37, No. 1, pp. 58-65.*
Hussein et al., Preparation and characterization of acive carbons from oil palm shells, 1996, Carbon, vol. 34, No. 11, pp. 1447-1449.*
Ahmadpour et al., The preparation of activated carbon from Macadamia nutshell by chemical activation, 1997, Carbon, vol. 35, No. 12, pp. 1723-1732.*
Caturla et al., Preparation of Activated Carbon by Chemical Activation with ZnCl2, 1991, Carbon, vol. 29, No. 7, pp. 999-1007.*
N. Nakamichi et al., "Oxidative Aromatization of 9,10-Dihydroanthracenes Using Molecular Oxygen Promoted by Activated Carbon", J. Org. Chem., vol. 68, No. 21, pp. 8272-8273, 2003.
Supplementary European Search Report issued Aug. 18, 2009 in connection with corresponding European Application No. 05 78 1566 in,the English language.
K. Sup Song et al. "Characteristics of Oxygen Chemisorption on Porous Coal Char", Korean Journal of Chemical Engineering, vol. 16, No. 2, pp. 175-179 (Mar. 1, 1999).
N.R. Laine et al. "The Importance of Active Surface Area in the Carbon-Oxygen Reaction", Journal of Physics and Chemistry, vol. 67, pp. 2030-2034 (Jun. 1, 1963).

* cited by examiner

*Primary Examiner*—Porfirio Nazario Gonzalez
*Assistant Examiner*—Yate K Cutliff
(74) *Attorney, Agent, or Firm*—Wenderoth, Lind & Ponack, LLP.

(57) ABSTRACT

It is a problem to be solved by the present invention to provide an oxidation catalyst which, in oxidation of a compound, can efficiently effect oxidation using oxygen in the air as an oxygen source and can be used repeatedly.

The above-mentioned problem was solved by an activated carbon in which the BET specific surface area S determined by a nitrogen adsorption method and the amount of surface oxygen which will leave in the form of carbon monoxide $O_{CO}$ (% by weight) satisfy formula (I) $4000 < S \times O_{CO}$. By using this oxidation catalyst, it is possible to oxidize a compound having an oxidizable carbon atom linked directly to an aromatic ring, including a heterocyclic ring, to a corresponding aldehyde or keto compound, or to oxidatively dehydrogenate a hydrogen-containing compound to form an unsaturated bond or a cyclic compound, or to oxidatively and dehydrogenatively form a nitrogen-containing heterocyclic ring from an aryl aldehyde and a compound having a pair of adjacent carbon atoms, one of the carbon atoms having an amino group and the other having an amino, hydroxyl or mercapto group.

3 Claims, No Drawings

US 7,893,004 B2

OXIDATION REACTION CATALYST AND PROCESS FOR PRODUCING A COMPOUND USING THE SAME

This application is a U.S. national stage of International Application No. PCT/PJ2005/016227 filed Sep. 5, 2005.

TECHNICAL FIELD

The present invention relates to an oxidation catalyst which can promote various oxidation reactions efficiently under mild conditions using oxygen or oxygen in the air, and to a method for producing a compound using the same. It relates, particularly, to an oxidation catalyst which comprises an activated carbon having a large specific surface area and containing many oxygen-containing functional groups which will leave in the form of carbon monoxide, and to a method for producing an oxidation product using the same.

BACKGROUND ART

Oxidation of organic compounds, which, like reduction, is one of the most important functional group conversion reactions in the field of organic synthesis, is extremely useful in reactions for synthesizing functional compounds such as medicines and dyes.

For example, a 2-aryl benzoxazole skeleton, which is included in the basic skeletons of medicines, such as antiinflammatory agents and anticancer agents, must have conventionally been synthesized from a 2-aminophenol derivative and a benzaldehyde derivative using a stoichiometric or excessive amount of oxidizing agent which tends to load to the environment, such as barium permanganate, lead tetraacetate and DDQ.

A carbonyl compound produced through oxidation of and corresponding to an alkylarene, which is a starting material to important compounds because of the capability of being converted easily into compounds with various types of functional groups, has conventionally needed use of a stoichiometric amount of oxidizing agent such as manganese dioxide, selenium dioxide and periodic acid. Although a method using oxygen in the air has also been researched, it needs N-hydroxyphthalimide, ruthenium complexes, cobalt-Schiff base complexes or the like as a catalyst.

A method for producing 4-oxyisophorone by oxidizing β-isophorone using oxygen or oxygen-containing gas in the presence of activated carbon and a nitrogen-containing heterocyclic base instead of using such toxic catalysts has been proposed (Japanese Unexamined Patent Application Publication No. 11-49717). Regarding the activated carbon, however, only ones with specific surface areas ranging widely from 30 to 2000 m²/g are disclosed. Its working examples refer only to "activated carbon from coconut shell for chromatography" and do not use any special ones. The reactions require the presence of a specific type of nitrogen-containing heterocyclic base and no particular references are made to catalytic actions on other reaction substrates.

DISCLOSURE OF THE INVENTION

Problem to be Solved by the Invention

It is an object of the present invention to provide a catalyst which can promote oxidation of various organic compounds using oxygen or oxygen in the air under safe and mild conditions without using an oxidizing agent which is toxic and tends to load to the environment, such as heavy metal compounds.

Means for Solving the Problems

Activated carbon has a property to adsorb various substances. Adsorption is a phenomenon in which the concentration of a substance in an interface is higher than the concentration of the substance in a bulk phase. On the surface of activated carbon, the concentration of a solute in a solvent is higher that in other portions. Due to this fact, it is possible to accelerate various organic synthesis reactions through addition of activated carbon.

In the case of a reaction of synthesizing a compound using oxygen as an oxidizing agent, a measure for distributing and dissolving oxygen in the air must be taken. The present inventors found that it is possible to increase the reaction efficiency by adding an activated carbon which has a large specific surface area and has a large surface oxygen amount to the reaction system. At that time, they found that it is possible to greatly improve the reactivity by use of an activated carbon having a large amount of surface oxygen which will leave in the state of carbon monoxide on being heated. They made further investigations to accomplish the present invention.

That is, the present invention relates to the following items:

(1) An oxidation catalyst consisting of an activated carbon which satisfies formula (I):

$$4000 < S \times (O_{CO}) \qquad (I)$$

wherein S represents a BET specific surface area (m²/g) and $O_{CO}$ represents a percent by weight of the amount of surface oxygen which will leave in the form of carbon monoxide to the activated carbon determined by the following method:

the method for determining $O_{CO}$:

about 3 g of activated carbon is weighed out and is placed in a quartz tube with an inner diameter of about 25 mm and a length of about 100 cm; the quartz tube is inserted into a temperature-controllable tube furnace, which is then heated from room temperature to 900° C. over 30 minutes and is held at that temperature for 30 minutes while nitrogen gas is caused to flow at a rate of 0.1 L/min; the whole portion of the gas exhausted during this process is collected and the quantity of carbon monoxide is determined with a gas chromatography equipped with a methane converter; then, the percent by weight of the quantity of the oxygen contained in the carbon monoxide to the quantity of the activated carbon is calculated;

(2) The oxidation catalyst according to item 1, wherein the activated carbon is an activated carbon chemically activated at 300-700° C.;

(3) The oxidation catalyst according to item 1 or 2 which is used for a reaction of oxidizing a compound having an oxidizable carbon atom linked directly to an aromatic ring, including a heterocyclic ring, to a corresponding aldehyde or keto compound;

(4) The oxidation catalyst according to item 1 or 2 which is used for an oxidation reaction of forming an unsaturated bond or a cyclic compound by oxidatively dehydrogenating a hydrogen-containing compound;

(5) The oxidation catalyst according to item 1 or 2 which is used for an oxidation reaction of oxidatively and dehydrogenatively forming a nitrogen-containing heterocyclic ring from an aryl aldehyde and a compound having a pair of adjacent carbon atoms, one of the carbon atoms having an amino group and the other having an amino, hydroxyl or mercapto group; and (6) A method for producing an oxidation reaction product comprising bringing an oxidizable organic compound into contact with oxygen in the presence of the oxidation catalyst recited in item 1.

The oxidation catalyst of the present invention, which consists of an activated carbon satisfying formula (I) $4000 < S \times O_{CO}$, can be prepared by activating raw charcoal at a temperature from 300 to 700° C., preferably from 320 to 700° C., with a chemically activating agent, such as phosphoric acid, zinc chloride and alkali metal hydroxide and then washing the resulting activated carbon with water, hydrochloric acid, nitric acid, or the like.

The raw material of the oxidation catalyst may be any material which can be used as a raw material of normal activated carbon. Plant-based materials, such as wood, sawdust, charcoal, charred wood powder, fruit shells such as coconut shell and walnut shell, seeds of fruits such as peach and plum, fruit shell charcoal, fruit seed charcoal, pulp production by-products, lignin wastewater, sugar manufacture waste and blackstrap molasses, mineral materials, such as peat, grass peat, brown coal, lignite, bituminous coal, anthracite, corks, coal tar, coal pitch, petroleum distillation residue and petroleum pitch, and other naturally-occurring materials such as seaweed and rayon; and synthetic materials, such as phenol resin, vinylidene chloride resin, acrylic resin and polyvinyl alcohol, may be used.

The BET specific surface area of the activated carbon is usually from 1000 to 2000 m²/g, and preferably from 1200 to 1800 m²/g.

The surface oxygen which will leave in the form of carbon monoxide on being heated in the presence of oxygen is believed to be present in the form of a carbonyl group, quinone or aldehyde on the surface of activated carbon. The more oxygen presents in such a form, the higher the catalytic activity on oxidation.

Many of activated carbons conventionally used as a catalyst are produced by the steam activation method. At temperature required in the stream activation method as high as 800-1000° C., functional groups such as those mentioned above cannot exist stably on the surface of the activated carbon.

Examples of conventional methods of increasing the amount of surface oxygen of an activated carbon include air (oxygen) oxidization and oxidization with an oxidizing agent such as nitric acid and hydrogen peroxide in a wet state or in a heated state. It, however, is known that only the number of functional groups (a carboxyl group, lactone, etc.) which will leave in the state of carbon dioxide increases in these methods. These methods are not proper for obtaining activated carbon with a large amount of oxygen which will leave in the state of carbon monoxide, which is an object of the instant catalytic reaction.

In order to produce an oxidation catalyst to be used in the present invention, it is desirable to conduct activation at normally 300-700° C., preferably 320-700° C., using an activating chemical agent such as phosphoric acid, zinc chloride and alkali metal hydroxide.

In the case where an oxidation catalyst of the present invention is produced by the phosphoric acid activation method, activation is conducted by mixing a raw material with about 30-95%, preferably 60-80% of phosphoric acid and then heating the mixture for a period of time of from about 20 minutes to about 10 hours, preferably from about 30 minutes to about 5 hours at 300-700° C. It is desirable to adjust the activation time to be somewhat long when the activation temperature is low, or alternatively, somewhat short when the activation temperature is high. Subsequently, washing is conducted by use of warm water (30-80° C.) in an amount of 5-200 times, preferably 10-100 times the amount of the activated carbon, followed by drying.

In the case of production by the zinc chloride activation method, it is possible to produce an activated carbon having a large amount of surface oxygen which will leave in the form of carbon monoxide by adjusting the highest achieving temperature into a range of from 300 to 550° C., preferably from 450 to 550° C. in the activation reaction. A higher heating temperature is not very desirable because it will result in a reduced amount of surface oxygen which will leave in the form of carbon monoxide. A lower heating temperature is also not very desirable because the activation reaction will not proceed sufficiently. When the zinc chloride concentration is from 40 to 70 w/w %, the amount of the aqueous zinc chloride solution to be used is from 0.4 to 4.0 times, preferably from 1.0 to 3.5 times, and more preferably from 1.5 to 3.5 times the amount of activated carbon, on the weight basis. If too much zinc chloride is used, the reaction with the raw material will proceed too much and the reaction mixture will be difficult in filtration, resulted in trouble in purification. On the other hand, use of too little zinc chloride is undesirable because it is impossible to obtain a sufficient specific surface area. The activation time is from about 20 minutes to about 10 hours, preferably from about 30 minutes to about 5 hours. It is desirable to adjust the activation time to be somewhat long when the activation temperature is low, or alternatively, somewhat short when the activation temperature is high.

By washing the resulting activated carbon by use of hydrochloric acid with a concentration of from 0.5 to 35% in an amount of from 2 to 100 times the amount of the activated carbon, subsequently washing with water normally in an amount of from 2 to 100 times and then drying at 80-250° C., preferably at 80-200° C., and more preferably at 80-150° C., it is possible to produce an oxidation catalyst. It is permitted to wash with nitric acid instead of hydrochloric acid.

When the raw material is calcined in the presence of an alkali metal hydroxide such as sodium hydroxide and potassium hydroxide, calcination is effected at 320-700° C. It is desirable to conduct the calcination by dividing it into a first calcination at a low temperature and a second calcination a high temperature.

The first calcination is conducted usually at 320-380° C., preferably at 330-380° C., and more preferably at 335-350° C. The calcination time, which may vary depending on the instrument to be used, is usually from about 10 minutes to about 20 hours, preferably from about 20 minutes to about 10 hours, and more preferably from about 40 minutes to about 5 hours. The calcination is performed advantageously in inactive gas, such as nitrogen gas, carbon dioxide, helium gas and flue gas. Use of nitrogen gas is convenient and economical. Examples of the alkali metal hydroxide include sodium hydroxide, potassium hydroxide and lithium hydroxide. Sodium hydroxide is particularly preferred. The using ratio, on the weight basis, of the alkali metal hydroxide to the raw material of activated carbon is usually from 0.5 to 10, preferably from 1 to 5, and more preferably from 2 to 4. In order to calcine an activated carbon raw material in the presence of an alkali metal hydroxide, it is permitted to mix an activated carbon raw material with a solid alkali metal hydroxide and then to heat the mixture. Alternatively, it is permitted also to melt an alkali metal hydroxide or prepare an aqueous solution of an alkali metal hydroxide, to mix the resultant with an activated carbon raw material, and then to heat the mixture.

In the second calcination, activation is conducted by subjecting the product obtained by the first calcination treatment to the second calcination treatment. The second calcination temperature is usually from 450 to 700° C., preferably from 470 to 680° C., and more preferably from 480 to 670° C. The calcination time is usually from about 10 minutes to about 20 hours, preferably from about 20 minutes to about 10 hours, and more preferably from about 30 minutes to about 5 hours.

It is desirable to adjust the time to be somewhat long when the calcination temperature is somewhat low, or alternatively, somewhat short when the calcination temperature is somewhat high.

Like the first calcination, the second calcination is effected advantageously in inert gas such as nitrogen gas, carbon dioxide gas, helium gas and flue gas. Nitrogen gas is preferably used. The activated carbon which has been activated through such calcination is washed, for example, with water to allow the alkali metal hydroxide to be removed, and then is dried.

When an activated carbon is used as a catalyst, it is usually pulverized. The particle diameter (median diameter) of the activated carbon pulverized, as measured by the laser scattering/diffraction method, is from 1 to 100 μm, preferably from 2 to 50 μm, and more preferably from 5 to 20 μm. For the pulverization, micropulverizers conventionally used, such as container-driven medium mills, e.g. ball mill, high-speed rotation mills, e.g. hammer mill, and air-stream pulverizers, e.g. jet mill, can be used. Although activated carbon can be used as a catalyst without being pulverized, the reaction time may become longer.

The amount of surface oxygen of an activated carbon is measured in the following method.

About 3 g of activated carbon is weighed out and is placed in a quartz tube with an inner diameter of about 25 mm and a length of about 100 cm. The quartz tube is inserted into a temperature-controllable tube furnace, which is then heated from room temperature to 900° C. over 30 minutes and is held at that temperature for 30 minutes while nitrogen gas is caused to flow at a rate of 0.1 L/min. The whole portion of the gas exhausted during this process is collected and the quantity of carbon monoxide is determined with a gas chromatography equipped with a methane converter. Then, the weight percent of the quantity of the oxygen contained in the gas to the quantity of the activated carbon is calculated.

The amount of surface oxygen which will leave in the form of carbon monoxide in an oxidation catalyst composed of an activated carbon of the present invention, which may vary depending on the specific surface area of the carbon atom, is preferably 2.0% by weight or more, more preferably 2.5% by weight or more, and most preferably 3.0% by weight or more based on the amount of the activated carbon. Theoretically speaking, the more the amount of the surface oxygen which will leave in the form of carbon monoxide, the more suitable it is as an oxidation catalyst. However, 5% by weight is sufficient enough in practice.

The value of $S \times (O_{CO})$ in formula (I) in the oxidation catalyst of the present invention is 4000 or more, more preferably 4200 or more, and even more preferably 4500 or more.

Theoretically speaking, the greater the value of $S \times (O_{CO})$, the more desirable it is as an oxidation catalyst. However, 10000 are sufficient enough in practice.

In an oxidation reaction using an oxidation catalyst of the present invention, an organic compound which is to be oxidized, in other words, a substrate used for synthesis of a compound using the catalyst of the present invention, is, if necessary, dissolved in a proper solvent e.g. benzene, toluene, xylene, mesityrene, acetic acid, propionic acid, butyric acid and dimethyl formamide. The oxidation catalyst of the present invention is then added thereto. Oxygen or air is then introduced into the reactor, so that the substrate is caused to contact with oxygen.

One typical example of the oxidation reaction of the present invention is a reaction of oxidizing a compound having an oxidizable carbon atom linked directly to an aromatic ring, including a heterocycle, e.g. an alkylarene, to a corresponding aldehyde or keto compound. Another typical reaction is a reaction of oxidatively dehydrogenating a hydrogen-containing compound to form an unsaturated bond or a cyclic compound. Still another typical reaction is a reaction of oxidatively and dehydrogenatively forming a nitrogen-containing heterocyclic ring from an aryl aldehyde and a compound having a pair of adjacent carbon atoms, one of the carbon atoms having an amino group and the other having an amino, hydroxyl or mercapto group.

More specific examples include oxidation of alkylarenes to corresponding aldehydes or ketones, oxidative aromatization (dehydrogenation) of dihydro- or tetrahydroaromatic compounds such as 9,10-dihydroanthracenes, 1,4-dihydropyridine derivatives and trisubstituted pyrazolines to aromatic compounds, and synthesis of 2-phenylbenzoxazoles from aminophenols and benzaldehyde (dehydrogenation).

The amount of the oxidation catalyst to be added, which depends on the type of the reaction, is usually from 0.1 to 200% by weight based on the substrate. In order to increase the reaction rate, it is more desirable to use the oxidation catalyst in an amount of from 50 to 200% by weight. The concentration of the oxygen with which a substrate is brought into contact is preferably within the range of from 0.1 to 100%, more preferably from 5 to 100%, and most preferably from 15 to 100%. If the oxygen concentration is low, the reaction will proceed slowly. The oxygen or air may be introduced into the reaction solution through a tube. It, however, is usually sufficient only to bring the reaction solution into contact with the air while stirring the reaction solution. The oxidation reaction of the present invention can be accelerated by heating the reaction system properly. The reaction temperature is usually from 50 to 150° C., and preferably from 80 to 130° C.

After the completion of the reaction, the reaction product, an unreacted substrate and the oxidation catalyst can be separated by filtration. Washing a separated oxidation catalyst with a solvent followed by drying it will allow the catalyst to be used again as an oxidation catalyst.

Effect of the Invention

The oxidation catalyst of the present invention is free from toxicities caused by heavy metal salts or the like and can provide a desired product oxidized in a satisfactory yield under mild conditions using oxygen in the air. It therefore can be used suitably in the synthesis of useful substances such as medicines and dyes.

BEST MODE FOR CARRYING OUT THE INVENTION

The present invention will be described concretely below with reference to Examples, Conventional Examples and Experimental Examples.

EXAMPLE 1

To 50 g of dry wood flour, 140 g of a 60 w/w % aqueous solution of zinc chloride was added, mixed well, and placed in a crucible, which was then covered with a lid.

This was placed in an electric furnace and was heated from 100 to 250° C. over 2 hours and from 250 to 530° C. over 1 hour, held at that temperature for 30 minutes, and then cooled. This was placed in a washing vessel with filter cloth and an aqueous solution prepared by diluting 50 ml of hydrochloric acid with 0.2 L of water was added thereto. Stirring and washing were continued for 2 hours and then the water was drained off. Subsequently, the residue was washed with water at 50° C. at a rate of 0.25 L/hour for 4 hours. The washed activated carbon was dried in an electric dryer held at 115±5° C. The dried activated carbon was pulverized with a ball mill. Thus, oxidation catalyst No. 1 was obtained.

EXAMPLE 2

Oxidation catalyst No. 2 was obtained in the same manner as Example 1 except for changing the addition amount of a 60 w/w % aqueous solution of zinc chloride to 95 g.

EXAMPLE 3

Oxidation catalyst No. 3 was obtained in the same manner as Example 1 except for changing the addition amount of a 60 w/w % aqueous solution of zinc chloride to 75 g.

EXAMPLE 4

Oxidation catalyst No. 4 was obtained in the same manner as Example 1 except for using pulverized coconut husk, 90% or more of which could pass through a screen mesh of 0.150 mm, as a raw material and changing the use amount of a 60 w/w % aqueous solution of zinc chloride to 95 g.

EXAMPLE 5

Oxidation catalyst No. 5 was obtained in the same manner as Example 4 except for changing the amount of a 60 w/w % aqueous solution of zinc chloride to 50 g.

EXAMPLE 6

One kilogram of carbonized coconut husk whose particle size was regulated to 1.7-0.25 mm and 3 kg of granular sodium hydroxide were mixed well mixed. In nitrogen stream, the mixture was subjected to a first calcination at 340° C. for 60 minutes and subsequently to a second calcination at 500° C. for 40 minutes. The activated carbon obtained was washed well with warm water to remove sodium hydroxide, and then dried. the dried activated carbon was pulverized with a ball mill. Thus, oxidation catalyst No. 6 was obtained.

EXAMPLE 7

Oxidation catalyst No. 7 was obtained in the same manner as Example 6 except for changing the second calcination conditions to 650° C. and 40 minutes.

EXAMPLE 8

To 500 g of wood flour, 1560 g of a 80 w/w % phosphoric acid was added, mixed well, and placed in a crucible, which was then covered with a lid. This was placed in an electric furnace and was heated from 100 to 250° C. over 2 hours and from 250 to 500° C. over 1 hour, held at that temperature for 30 minutes, and then cooled. This was placed in a washing vessel with filter cloth and washed with water at 50° C. at a rate of 0.25 L/hour for 4 hours. The washed activated carbon was dried in an electric dryer held at 115±5° C. The dried activated carbon was pulverized with a ball mill. Thus, oxidation catalyst No. 8 was obtained.

EXAMPLE 9

Oxidation catalyst No. 9 was obtained in the same manner as Example 12 except for changing the amount of a 80 w/w % phosphoric acid to 1875 g.

COMPARATIVE EXAMPLE 1

Oxidation catalyst No. 8 was obtained in the same manner as Example 1 except for using calcination conditions of heating from 100 to 250° C. over 2 hours and from 250 to 600° C. over 1 hour and holding at that temperature for 30 minutes.

COMPARATIVE EXAMPLE 2

Oxidation catalyst No. 11 was obtained in the same manner as Example 1 except for changing the use amount of a 60 w/w % aqueous solution of zinc chloride to 35 g.

COMPARATIVE EXAMPLE 3

Daxi coal produced in Shanxi Province, China was used as a raw material. This charcoal was pulverized and regulated to a particle diameter within the range of from 2.36 to 1.18 mm. It was heated to 350-550° C. over 1 hour and then was subjected to stream-activation at 850° C. for 5 hours. The activated carbon was washed with hydrochloric acid and then with warm water, and subsequently pulverized with a ball mill. Thus, oxidation catalyst No. 12 was obtained.

COMPARATIVE EXAMPLE 4

Oxidation catalyst No. 13 was obtained in the same manner as Example 8 except for changing the amount of 80 w/w % phosphoric acid to 250 g.

COMPARATIVE EXAMPLE 5

Oxidation catalyst No. 14 was obtained in the same manner as Example 6 except for further effecting a heat treatment at 850° C. for 30 minutes under nitrogen stream after the two-step calcination of Example 6.

For each of the oxidation catalysts obtained in Examples and Comparative Examples, the specific surface area S and the amount of oxygen which leaves in the form of carbon monoxide, $O_{CO}$, were measured and are shown in Table 1.

TABLE 1

| | Oxidation catalyst | | | | | | | | |
| --- | --- | --- | --- | --- | --- | --- | --- | --- | --- |
| | No. 1 Example 1 | No. 2 Example 2 | No. 3 Example 3 | No. 4 Example 4 | No. 5 Example 5 | No. 6 Example 6 | No. 7 Example 7 | No. 8 Example 8 | No. 9 Example 9 |
| Raw materials | Wood flour | Wood flour | Wood flour | Coconut husk | Coconut husk | Coconut husk | Coconut husk | Wood flour | Wood flour |
| Activation method | Zinc chloride | Zinc chloride | Zinc chloride | Zinc chloride | Zinc chloride | NaOH | KOH | Phosphoric acid | Phosphoric acid |
| S (m²/g) | 1455 | 1423 | 1279 | 1420 | 1245 | 1494 | 2003 | 1487 | 1758 |

TABLE 1-continued

| | | | | | | | | | |
|---|---|---|---|---|---|---|---|---|---|
| Oxidation catalyst | | | | | | | | | |
| $O_{CO}$ | 3.13 | 3.03 | 3.14 | 2.95 | 3.25 | 2.95 | 2.64 | 2.8 | 2.78 |
| $S \times O_{CO}$ | 4555 | 4312 | 4016 | 4189 | 4046 | 4407 | 5288 | 4223 | 4887 |

| | No. 10 Comparative Example 1 | No. 11 Comparative Example 2 | No. 12 Comparative Example 3 | No. 13 Comparative Example 4 | No. 14 Comparative Example 5 |
|---|---|---|---|---|---|
| Raw materials | Wood flour | Wood flour | Coal | Wood flour | Coconut husk |
| Activation method | Zinc chloride | Zinc chloride | Steam | Phosphoric acid | NaOH |
| S (m²/g) | 1510 | 1120 | 1240 | 945 | 1426 |
| $O_{CO}$ | 2.35 | 3.08 | 1.87 | 2.95 | 1.21 |
| $S \times O_{CO}$ | 3549 | 3450 | 2319 | 2788 | 1725 |

TEST EXAMPLE 1

Synthesis of 2-(p-methoxyphenol)benzoxazole 873 mg (8 mmol) of 2-aminophenol, 1089 mg (8 mmol) of p-anisaldehyde, 1 g of an oxidation catalyst and 15 ml of xylene as solvent were charged into a 100 ml three-neck flask and were stirred at 120° C. for 4 hours under an oxygen atmosphere. After the confirmation of the completion of oxidation, the reaction mixture was filtered through Celite and the Celite was washed with a small amount of ethyl acetate. After the filtrate and the washings were combined and condensed to about 2 ml with a rotary evaporator, the product was separated by silica gel column chromatography. A resulting pale yellow crystalline solid was weighed and the yield thereof was defined as a reaction yield.

TEST EXAMPLE 2

Synthesis of 1,3,5-triphenylpyrazole 1,3,5-Triphenylpyrazoline (300 mg, 1.01 mmol), 150 mg of an oxidation catalyst and acetic acid (3.5 ml) were charged into a 100 ml three-neck flask, and were stirred at 120° C. for 2.5 hours under an oxygen atmosphere. The reaction mixture was filtered through Cerite. The filtrate was poured into a saturated aqueous solution of sodium hydrogencarbonate and then was extracted with ethyl acetate. The extract was condensed and 1,3,5-triphenylpyrazole was obtained as a pale yellow solid by means of silica gel column chromatography.

TEST EXAMPLE 3

Synthesis of 2-phenylbenzimidazole

2-Phenylenediamine (951 mg, 8.8 mmol), 1 g of an oxidation catalyst and 10 ml of xylene as solvent were charged into a 100 ml three-neck flask. The substrate was dissolved by stirring at 120° C. for 30 minutes and then a mixed solution of benzaldehyde (0.813 ml, 8 mmol) and xylene (5 ml) was added thereto slowly over 1 hour under an oxygen atmosphere, followed by stirring for 1 hour. The reaction mixture was filtered through Celite, and then the Celite and the oxidation catalyst were washed with ethyl acetate. The filtrate was condensed with a rotary evaporator to yield a solid. The solid was recrystallized from ethyl acetate. Resulting pale yellowish brown crystals were then weighed and the yield thereof was defined as a reaction yield.

TEST EXAMPLE 4

Synthesis of 2-phenylbenzothiazole

2-Aminothiophenol (0.856 ml, 8 mmol), benzaldehyde (0.813 ml, 8 mmol), 1 g of an oxidation catalyst and 15 ml of xylene as solvent were charged into a 100 ml three-neck flask, and were stirred at 120° C. for 13 hours under an oxygen atmosphere. The reaction mixture was filtered through Celite, and then the Celite and the oxidation catalyst were washed with ethyl acetate. The filtrate was condensed with a rotary evaporator to yield a solid. The solid was recrystallized from diethyl ether. Resulting colorless crystals were then weighed and the yield thereof was defined as a reaction yield.

TEST EXAMPLE 5

Synthesis of 2-phenyl-4(1-methylethyl)oxazoline

L-Valinol (206 mg, 2 mmol), benzaldehyde (0.205 ml, 2 mmol), 250 mg of an oxidation catalyst and 4 ml of xylene as solvent were charged into a 100 ml three-neck flask, and were stirred at 150° C. for 67 hours under an oxygen atmosphere. The reaction mixture was filtered through a cotton plug, and then the oxidation catalyst was washed with ethyl acetate. After the filtrate was condensed with a rotary evaporator, the product was separated by silica gel column chromatography. A resulting colorless liquid was weighed and the yield thereof was defined as a reaction yield.

TEST EXAMPLE 6

Synthesis of Fluorenone

Fluorene (524 mg, 3.15 mmol), 524 mg of an oxidation catalyst and 5 ml of xylene as solvent were charged into a 100 ml three-neck flask, and were stirred at 120° C. for 24 hours under an oxygen atmosphere. The reaction mixture was filtered through Celite, and then the Celite and the oxidation catalyst were washed with ethyl acetate. After the filtrate was condensed with a rotary evaporator, the product was separated by silica gel column chromatography. A resulting yellow crystalline solid was weighed and the yield thereof was defined as a reaction yield.

The reaction yields in Test Examples 1 through 6 are shown in Table 2.

TABLE 2

Results of reactions using oxidation catalysts

|  | No. 1 Example 1 | No. 2 Example 2 | No. 3 Example 3 | No. 4 Example 4 | No. 5 Example 5 | No. 6 Example 6 | No. 7 Example 7 | No. 8 Example 8 | No. 9 Example 9 |
|---|---|---|---|---|---|---|---|---|---|
| Test Example 1 (%) | 78 | 69 | 63 | 68 | 66 | 75 | 92 | 68 | 82 |
| Test Example 2 (%) | 91 | 76 | 74 | 72 | 74 | 89 | 98 | 77 | 93 |
| Test Example 3 (%) | 80 | 75 | 68 | 73 | 65 | 77 | 89 | 71 | 86 |
| Test Example 4 (%) | 74 | 68 | 65 | 65 | 63 | 71 | 86 | 66 | 81 |
| Test Example 5 (%) | 84 | 81 | 75 | 80 | 76 | 85 | 98 | 81 | 94 |
| Test Example 6 (%) | 74 | 73 | 68 | 71 | 67 | 73 | 91 | 74 | 89 |

|  | No. 10 Comparative Example 1 | No. 11 Comparative Example 2 | No. 12 Comparative Example 3 | No. 13 Comparative Example 4 | No. 14 Comparative Example 5 |
|---|---|---|---|---|---|
| Test Example 1 (%) | 55 | 51 | 35 | 45 | 28 |
| Test Example 2 (%) | 62 | 58 | 41 | 52 | 34 |
| Test Example 3 (%) | 58 | 52 | 30 | 48 | 31 |
| Test Example 4 (%) | 52 | 51 | 28 | 34 | 21 |
| Test Example 5 (%) | 60 | 54 | 41 | 48 | 27 |
| Test Example 6 (%) | 59 | 57 | 38 | 41 | 24 |

In Examples 1 through 9 where oxidation catalysts Nos. 1 through 9 of the present invention were used, in each of Experimental Examples 1 through 6, the reaction yield was as high as 65% or more. On the other hand, in Comparative Examples 1 through 4 using oxidation catalysts Nos. 10 through 14, the yield was as low as 80% or less of that of the corresponding Example. In other words, the $S \times (O_{CO})$ values were smaller than 4000 and the yields of oxidation reaction were low because, in Comparative Examples 1, 3 and 5, the $O_{CO}$ amounts were small though the specific surface areas were large and because, in Comparative Examples 2 and 4, the specific surface areas were small though the $O_{CO}$ amounts were large.

TEST EXAMPLE 7

Reuse of Oxidation Catalysts

In the reaction of Test Example 1, a reaction was performed using the catalyst of Example 1, followed by centrifugal separation of the content fluid and collection of the supernatant instead of filtration of the content fluid. The remaining oxidation catalyst was washed with 5 ml of acetone repeatedly four times and then the resulting oxidation catalyst was dried in a dryer at 60° C.

Thereafter, 2-aminophenol (873 mg, 8 mmol), benzaldehyde (849 mg, 8 mmol) and 15 ml of xylene as solvent were added and a reaction was conducted in a similar manner. The reaction yield was 79% and a result almost the same as that of the first reaction was obtained. When the same operation was repeated three times, there was no decrease in reaction yield.

It was found from this fact that this oxidation catalyst can be used repeatedly.

INDUSTRIAL APPLICABILITY

The oxidation catalyst of the present invention is free of toxicity and can be used for reactions using oxygen in the air, for example, a reaction of oxidizing a compound having an oxidizable carbon atom linked directly to an aromatic ring, including a heterocyclic ring, to a corresponding aldehyde or keto compound, a reaction of forming an unsaturated bond or a cyclic compound by oxidatively dehydrogenating a hydrogen-containing compound, and a reaction of oxidatively and dehydrogenatively forming a nitrogen-containing heterocyclic ring from an aryl aldehyde and a compound having a pair of adjacent carbon atoms, one of the carbon atoms having an amino group and the other having an amino, hydroxyl or mercapto group. The oxidation catalyst can be used for synthesis of medicines, dyes, etc.

The invention claimed is:

1. An oxidation catalyst comprising an activated carbon which satisfies formula (I):

$$4000 < S \times (Oco) \tag{I}$$

wherein S represents a BET specific surface area (m²/g) and Oco represents a percent by weight of the amount of surface oxygen which will leave in the form of carbon monoxide to the activated carbon determined by the following method:

the method for determining Oco:

about 3 g of activated carbon is weighed out and is placed in a quartz tube with an inner diameter of about 25 mm and a length of about 100 cm; the quartz tube is inserted into a temperature-controllable tube furnace, which is then heated from room temperature to 900° C. over 30 minutes and is held at that temperature for 30 minutes while nitrogen gas is caused to flow at a rate of 0.1 L/min; the whole portion of the gas exhausted during this process is collected and the quantity of carbon monoxide is determined with a gas chromatography equipped with a methane converter; then, the percent by weight of the quantity of the oxygen contained in the carbon monoxide to the quantity of the activated carbon is calculated.

2. The oxidation catalyst according to claim 1, wherein the activated carbon is an activated carbon chemically activated at 300-700° C.

3. A method for producing an oxidation reaction product comprising bringing an oxidizable organic compound into contact with oxygen in the presence of the oxidation catalyst recited in claim 1.

* * * * *